(12) United States Patent
Singh-Gasson et al.

(10) Patent No.: US 6,315,958 B1
(45) Date of Patent: Nov. 13, 2001

(54) FLOW CELL FOR SYNTHESIS OF ARRAYS OF DNA PROBES AND THE LIKE

(75) Inventors: Sangeet Singh-Gasson, Mundelein, IL (US); Yongjian Yue, Sichuan (CN); Roland D. Green, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/437,369

(22) Filed: Nov. 10, 1999

(51) Int. Cl.[7] .................................................. C12M 1/00
(52) U.S. Cl. ................. 422/102; 422/99; 435/6; 435/7.1
(58) Field of Search .................. 422/50, 70, 99, 422/100, 102, 103; 435/6, 7.1; 436/578

(56) References Cited

U.S. PATENT DOCUMENTS

| | | | |
|---|---|---|---|
| 4,027,983 | * | 6/1977 | Abrahams ............................. 356/246 |
| 4,152,591 | * | 5/1979 | Averitt et al. ........................ 356/246 |
| 4,531,404 | * | 7/1985 | Phelps et al. ........................ 277/614 |
| 4,857,273 | * | 8/1989 | Stewart ................................ 422/68 |
| 4,877,747 | * | 10/1989 | Stewart ................................ 422/57 |
| 5,324,483 | | 6/1994 | Cody et al. . |
| 5,373,620 | * | 12/1994 | Zine et al. .......................... 29/469.5 |
| 5,399,317 | * | 3/1995 | Stolowitz ............................. 422/99 |
| 5,578,388 | | 11/1996 | Faita et al. . |
| 5,597,464 | | 1/1997 | Saur . |
| 5,677,195 | | 10/1997 | Winkler et al. . |
| 5,707,502 | | 1/1998 | McCaffrey . |

FOREIGN PATENT DOCUMENTS

| | | |
|---|---|---|
| 11046752 | 2/1999 | (JP) . |
| WO 98/52031 | 11/1998 | (WO) . |
| WO 99/00655 | 1/1999 | (WO) . |
| WO 99/42813 | 8/1999 | (WO) . |
| WO 99/52633 | 10/1999 | (WO) . |

* cited by examiner

*Primary Examiner*—Jill Warden
*Assistant Examiner*—Yelena Gakh
(74) *Attorney, Agent, or Firm*—Foley & Lardner

(57) ABSTRACT

A flow cell which can be used in the synthesis of DNA probes on an active surface of the substrate includes a base having a central window opening and a registration surface against which the substrate may be mounted. A gasket having a central opening defining an active area is mounted on the active surface of the substrate and has inlet and output extension openings which extend away from the central opening. A press block is engaged against the gasket to fully enclose an active volume between the press block, the peripheral walls of the central opening in the gasket, and the active surface of the substrate. A press is mounted to the base to selectively press the press block against the gasket and hold it in position. Channels in the press block extend to the extension openings in the gasket to allow flow of reagent into and out of the active volume, which is confined to the thickness of the gasket and can thus be minimized. The press may include a press screw which can be turned to engage against the press block to hold it into position, and which can be turned to release the press block from the gasket, allowing rapid and easy replacement of substrates.

21 Claims, 3 Drawing Sheets

FLOW CELL FOR SYNTHESIS OF ARRAYS OF DNA PROBES AND THE LIKE

FIELD OF THE INVENTION

This invention pertains generally to the field of biology and particularly to apparatus for use in the analysis and sequencing of DNA and related polymers.

BACKGROUND OF THE INVENTION

The sequencing of deoxyribonucleic acid (DNA) is a fundamental tool of modern biology and is conventionally carried out in various ways, commonly by processes which separate DNA segments by electrophoresis. See, e.g., Current Protocols In Molecular Biology, Vol. 1, Chapter 7, "DNA Sequencing," 1995. The sequencing of several important genomes has already been completed (e.g., yeast, *E. coli*), and work is proceeding on the sequencing of other genomes of medical and agricultural importance (e.g., human, *C. elegans,* Arabidopsis). In the medical context, it will be necessary to "re-sequence" the genome of large numbers of human individuals to determine which genotypes are associated with which diseases. Such sequencing techniques can be used to determine which genes are active and which inactive either in specific tissues, such as cancers, or more generally in individuals exhibiting genetically influenced diseases. The results of such investigations can allow identification of the proteins that are good targets for new drugs or identification of appropriate genetic alterations that may be effective in genetic therapy. Other applications lie in fields such as soil ecology or pathology where it would be desirable to be able to isolate DNA from any soil or tissue sample and use probes from ribosomal DNA sequences from all known microbes to identify the microbes present in the sample.

The conventional sequencing of DNA using electrophoresis is typically laborious and time consuming. Various alternatives to conventional DNA sequencing have been proposed. One such alternative approach, utilizing an array of oligonucleotide probes synthesized by photolithographic techniques is described in Pease, et al., "Light-Generated Oligonucleotide Arrays for Rapid DNA Sequence Analysis," Proc. Natl. Acad. Sci. USA, Vol. 91, pp. 5022–5026, May 1994. In this approach, the surface of a solid support modified with photolabile protecting groups is illuminated through a photolithographic mask, yielding reactive hydroxyl groups in the illuminated regions. A 3' activated deoxynucleoside, protected at the 5' hydroxyl with a photolabile group, is then provided to the surface such that coupling occurs at sites that had been exposed to light. Following capping, and oxidation, the substrate is rinsed and the surface is illuminated through a second mask to expose additional hydroxyl groups for coupling. A second 5' protected activated deoxynucleoside base is presented to the surface. The selective photodeprotection and coupling cycles are repeated to build up levels of bases until the desired set of probes is obtained. It may be possible to generate high density miniaturized arrays of oligonucleotide probes using such photolithographic techniques wherein the sequence of the oligonucleotide probe at each site in the array is known. These probes can then be used to search for complementary sequences on a target strand of DNA, with detection of the target that has hybridized to particular probes accomplished by the use of fluorescent markers coupled to the targets and inspection by an appropriate fluorescence scanning microscope. A variation of this process using polymeric semiconductor photoresists, which are selectively patterned by photolithographic techniques, rather than using photolabile 5' protecting groups, is described in McGall, et al., "Light-Directed Synthesis of High-Density Oligonucleotide Arrays Using Semiconductor Photoresists," Proc. Natl. Acad. Sci. USA, Vol. 93, pp. 13555–13560, Nov. 1996, and G. H. McGall, et al., "The Efficiency of Light-Directed Synthesis of DNA Arrays on Glass Substrates," Journal of the American Chemical Society 119, No. 22, 1997, pp. 5081–5090.

A disadvantage of both of these approaches is that four different lithographic masks are needed for each monomeric base, and the total number of different masks required are thus four times the length of the DNA probe sequences to be synthesized. The high cost of producing the many precision photolithographic masks that are required, and the multiple processing steps required for repositioning of the masks for every exposure, contribute to relatively high costs and lengthy processing times.

An improved process for synthesizing arrays of DNA probe sequences, polypeptides, and the like, rapidly and efficiently by a patterning process utilizing a computer controlled image former, is described in published PCT application International Publication No. WO 99/42813, published Aug. 26 1999, entitled Method and Apparatus for Synthesis of Arrays of DNA Probes. This process eliminates the need for a lithographic mask, significantly reducing the costs and time delays that have been associated with processes requiring such masks. In the patterning process described in the foregoing published PCT application, a substrate with an active surface to which, e.g., DNA synthesis linkers have been applied, is used to support probes to be activated. To activate the surface a high precision two-dimensional light image is projected onto the substrate by an image former, illuminating those pixels on the active surface which are to be activated to bind a first base. The light incident on the pixels in the array to which the light is applied deprotects OH groups and makes them available for binding the bases. After this development step, a fluid containing the appropriate base is provided to the active surface of the substrate and the selected base binds to the exposed sites. The process is repeated until all of the elements of the two-dimensional array on the substrate surface have an appropriate base bound thereto. The process is repeated for other pixel locations and desired levels of bases until the entire selected two-dimensional array of probe sequences has been completed. To provide the various chemicals in an appropriate sequence to the substrate, the substrate may be mounted within a flow cell having an enclosure which seals off the active surface of the substrate, allowing the appropriate reagents to flow through the flow cell and over the active surface.

SUMMARY OF THE INVENTION

The present invention is directed to an improved flow cell of the type that may be utilized in the synthesis of arrays of DNA probe sequences, polypeptides and the like, and is particularly adapted to be used with image formers for projecting an array of patterned light onto a substrate held by the flow cell. The flow cell of the invention is formed to precisely align a substrate with respect to an image former while distributing the fluid containing the appropriate chemicals through the active volume and over the active exposed surface of the flow cell, while minimizing the total volume of fluid contained within the flow cell to conserve the reagents being utilized. The flow cell allows fast and simple removal and replacement of substrates while insuring a tight seal around the substrate to minimize the leakage of reagents in the flow cell, and it locates the active surface of the substrate at the focal plane of the image former with a high degree of accuracy and repeatability.

A flow cell of a preferred construction in accordance with the invention includes a base having a central window opening and a registration surface against which a substrate may be mounted with its active surface opposite to that which is engaged against the registration surface. A gasket having a central opening defining an active area surrounded by the material of the gasket is mounted on the active surface of the substrate. The gasket has inlet and outlet extension openings which optionally and preferably extend away from the central opening in the gasket. A press block has an engagement surface which is adapted to the engaged against the gasket to fully enclose an active volume between the press block, the peripheral walls of the central opening in the gasket, and the active surface of the substrate. A press mounted to the base is formed to selectively press the press block against the gasket and hold it in position. The press block preferably includes a channel therein which extends from an exterior surface of the press block to a position in communication with the inlet opening extension in the gasket and another channel extending from the exterior surface of the press block to communication with the outlet extension opening in the gasket, thereby allowing reagents to flow into the active volume between the inlet opening extension and the outlet opening extension across the active surface area defined by the central opening in the gasket. The registration surface of the base is preferably raised above adjacent areas of the base and surrounds the central window opening to define a flat plane. The plane of the registration surface is utilized to precisely locate the active surface of the substrate with respect to an optical image former which projects an image through the window opening of the base and through a transparent substrate to a focal plane at the active surface of the substrate. The gasket is preferably formed of a thin non-reactive material having parallel flat surfaces. The thin gasket allows the active volume within the flow cell through which reagents flow to be minimized, with the extension openings in the gasket allowing inlet and outlet of the reagent into and out of the active volume in a manner which allows substantially the full central opening area of the gasket to be utilized as the active volume, with uniform flow of reagent across the active volume.

A press structure is preferably utilized to selectively press the press block against the gasket and the substrate. The press structure includes a standing frame secured to the base and having an upright section and an arm section which extends therefrom over the central opening in the base. A press screw is threadingly engaged with the arm and has a drive end positioned to engage an external surface of the press block as the press screw is turned to thread it toward the press block. The drive end is preferably rounded and fits into a rounded concave depression in the press block to provide a ball-and-socket engagement between the press screw and the press block that allows the press block to seat against the gasket and provide even pressure by the press block over the entire surface area of the gasket. When a substrate is to be changed, the press screw can be easily unscrewed by the operator until the press block is free of the press screw, allowing the press block and substrate to be removed, a new substrate to be inserted into position and the gasket and press block repositioned onto the active substrate, after which the press screw can be threaded down into contact with the press block to drive it into engagement with the gasket to seal the active volume in the flow cell.

Further objects, features and advantages of the invention will be apparent from the following detailed description when taken in conjunction with the accompanying drawings.

DETAILED DESCRIPTION OF THE INVENTION

Figure 1:
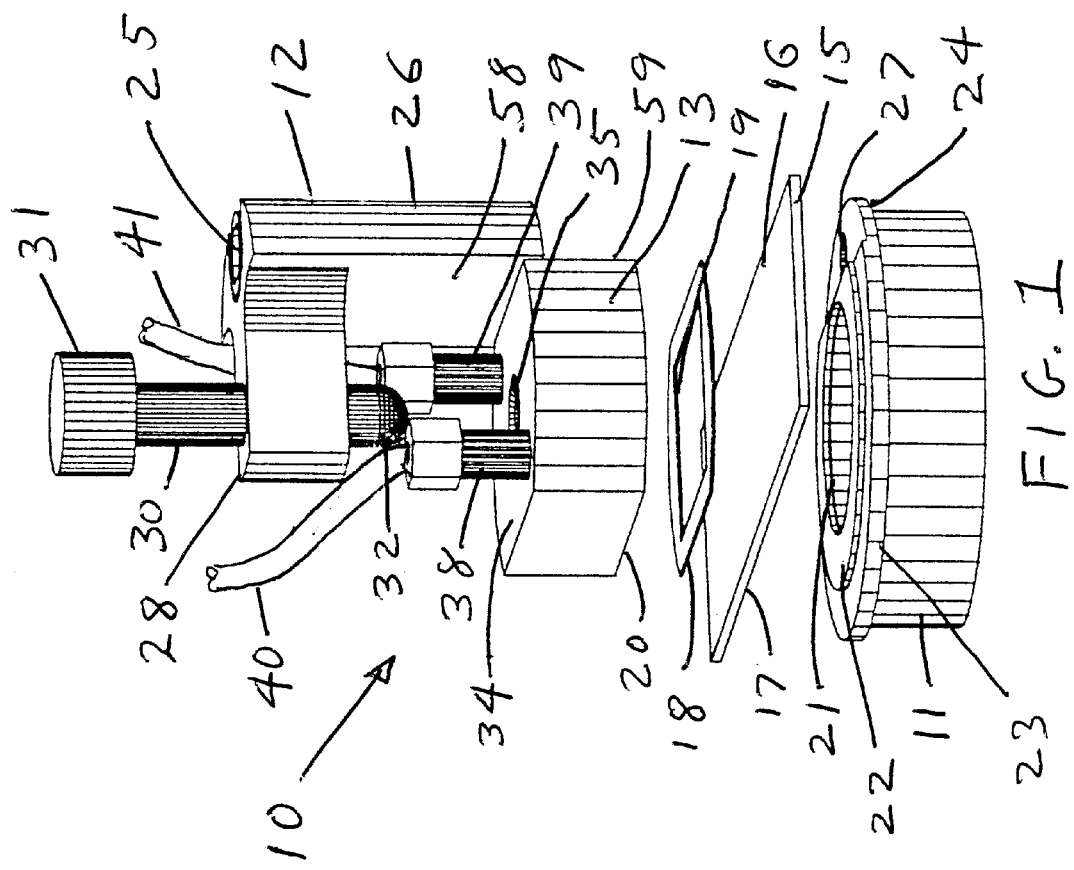
FIG. 1 is an exploded perspective view of the flow cell of the present invention showing the parts separated and in position for assembly.

With reference to the drawings, an exploded view of a flow cell in accordance with the invention in position for assembly is shown generally at 10 in FIG. 1. The flow cell 10 includes a base 11, a standing frame 12 which is secured to the base (and may be integrally formed therewith), and a press block 13. A substrate 15, typically a transparent glass slide, has two parallel flat surfaces 16 and 17, with one of the surfaces 16 forming an active surface of the substrate. A gasket 18 having a central opening 19 is mounted between the substrate 15 and the press block 13 and is pressed between the active surface 16 of the substrate and an engagement surface 20 of the press block when the flow cell is in use.

The base 11 is preferably formed of a solid piece of material, e.g., aluminum, having a central window opening 21 which is surrounded by a registration surface 22 which is preferably raised above the adjacent surfaces of the base. The registration surface 22 is preferable machined to be flat to a high degree of precision so that when the surface 17 of the substrate 15 is mounted in engagement with the registration surface 22, the parallel active surface 16 of the substrate will be precisely located with respect to a light image projected by an image former (not shown) through the window opening 21 of the base onto a focal plane which should be located at and parallel to the active surface 16. The image former may be of the type described in the published PCT application WO 99/42813, although it is understood that the use of the flow cell 10 is not limited to such systems. The base 11 has an outwardly extending rim 23 with a flat reference surface 24 on the underside of the rim 23 that is parallel to the registration surface 22. When the reference surface 24 is engaged against a surface of a mounting ring (not shown) of the image former having a known location in the image former, the registration surface 22 will thereby be located in proper position with respect to the image former.

Figure 2:
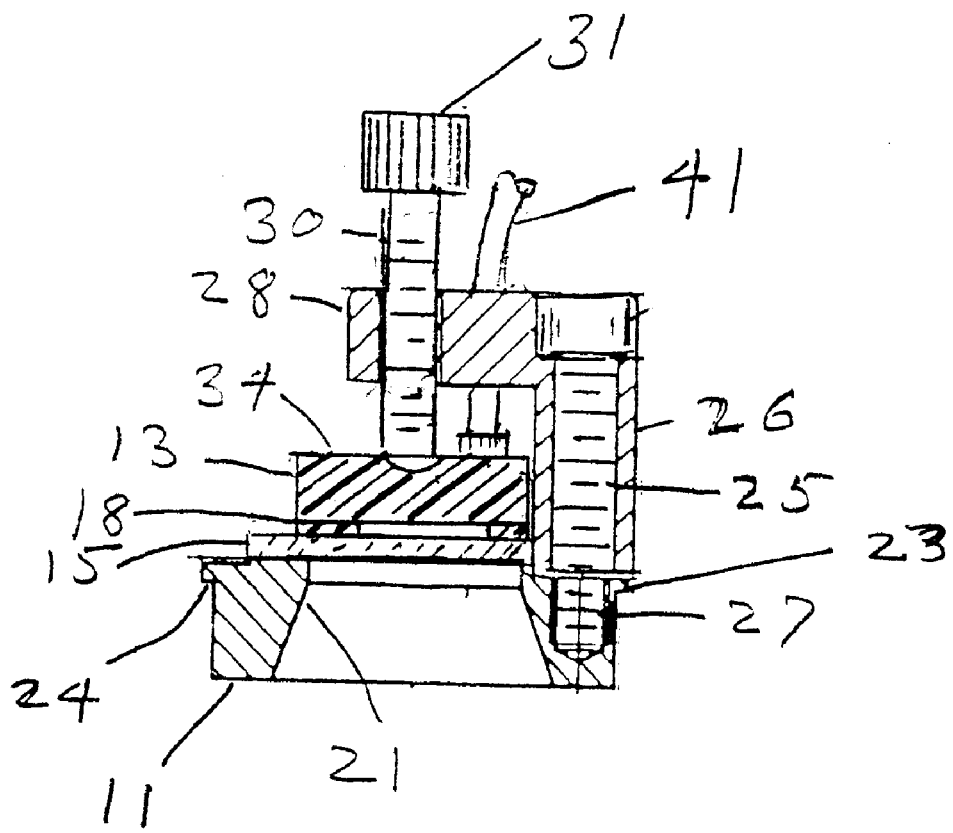
FIG. 2 is a cross sectional view through the assembled flow cell of the invention.
Figure 3:
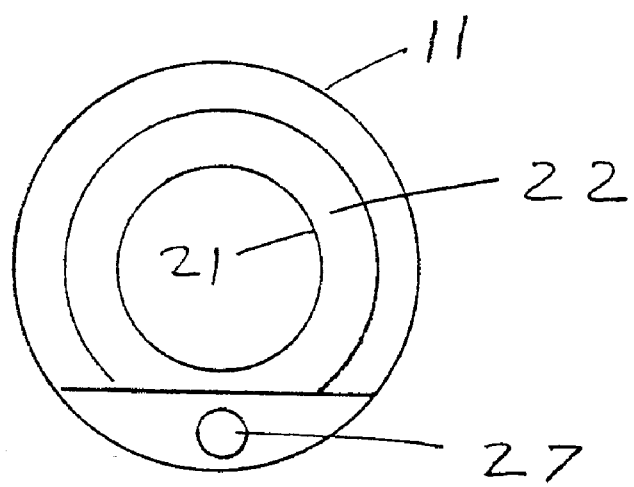
FIG. 3 is a top view of the base of the flow cell.

The standing frame 12 is secured to the base 11, as by a set screw 25 which threads through a threaded bore in an upright section 26 of the standing frame 12 and into a threaded blind hole 27 in the base, as best shown in the cross sectional view of FIG. 2. The standing frame 12 may also be formed integrally with the base or may be secured to the base by any other means, e.g., by a clamp, etc. An arm section 28 of the standing frame extends outwardly from the upright section 26 and, when the standing frame is mounted to the base, over the central opening 21 in the base. A press screw 30 is threadingly engaged to the arm 28 through a threaded bore in the arm and has an expanded head 31 which is adapted to be grasped and turned by a user. The press screw 30 terminates in a drive end 32 which is preferably rounded as shown. The standing frame 12 with the drive screw 30 engaged therewith forms a press which, when the standing frame is secured to the base 11, is adapted to selectively apply pressure to the press block 13 to engage it tightly against the gasket 18 so that the gasket is held tightly between the press block 13 and the substrate 15. Although not preferred, other means may be used to press the press block against the gasket, e.g., a C-clamp, screw(s) threaded between the press block and base, spring-loaded clamps, etc. The use of the press screw 30 is preferred because it provides a one point type pressing system to exert a uniform pressure and thereby ensure good sealing.

The press block 13 has a top external surface 34, opposite the engagement surface 20, which has formed therein a concave rounded depression 35 which is positioned to receive a rounded drive end 32 of the press screw 30. When the press block 13 is in its assembled position, as best shown in the cross sectional view of FIG. 2, the press screw 30 may be turned by the user to draw it downwardly such that the drive end 32 fits into the depression 35 to engage therewith with a ball-and-socket arrangement so that the press block 13 can seat itself against the gasket 18, applying uniform pressure throughout the area of the gasket. The engagement of the press screw 32 with the depression 35 also helps to center the press block in its proper position.

Figure 4:
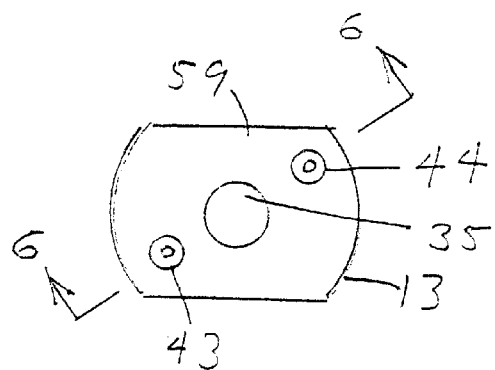
FIG. 4 is a top view of the press block of the flow cell.
Figure 5:
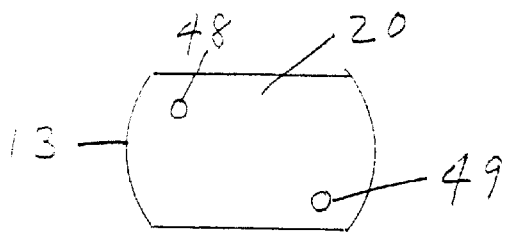
FIG. 5 is a bottom view of the press block.
Figure 6:
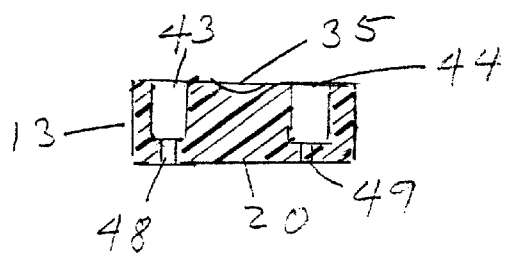
FIG. 6 is a cross sectional view of the press block taken generally along the line 6—6 of FIG. 4.
Figure 7:
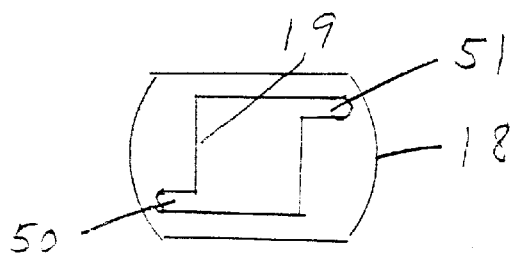
FIG. 7 is a plan view of a preferred gasket for use in the flow cell of the invention.

The press block 13 has an inlet fitting 38 and an outlet fitting 39 engaged to the press block at the top surface 34. The fittings 38 and 39 are connected to supply tubes 40 and 41 by which reagent may be supplied to and removed from the flow cell. As best shown in the top and bottom views of FIG. 4 and 5 and the cross sectional view of FIG. 6, the press block 13 has threaded bores 43 and 44 formed in its top surface 34 into which the fittings 38 and 39 are threadingly engaged, with the bores 43 and 44 terminating at a position above the bottom surface 19, with an inlet channel 48 and an outlet channel 49 extending through the press block from the bores 43 and 44 to define and an inlet channel and an outlet channel, respectively. As best shown in FIG. 7, the central opening 19 in the gasket 18 defines an active area (which may be square or rectangular as shown), with an inlet extension opening 50 and an outlet extension opening 51 formed in the gasket which extend outwardly from the central opening 19 in the gasket. When the gasket 18 is mounted in place on the substrate with the press block 13 engaged with it, the inlet channel 48 in the press block will be in communication with the inlet opening extension in the gasket, and the outlet channel 49 will be in communication with the outlet extension opening 51 in the gasket. Reagent flowing in through the inlet channel 48 will pass into the region defined by the extension opening 50 and then through and across the central opening 19 in the gasket to the outlet extension opening 51, and from thence to the outlet channel 49.

The entire active volume of the flow cell is defined between the periphery of the central opening in the gasket, acting as the side walls of the active volume, and the engagement surface 20 of the press block at the top and the substrate active surface 16 at the bottom. This active volume can be made very small while still insuring ample flow of reagent across the entire active area by utilizing a thin gasket 18 with parallel bottom and top surfaces. For example, the gasket, which may be formed of a non-reactive plastic or synthetic material such as Kalrez® perfluoroelastomer from DuPont Dow elastomers, may have a thickness of, e.g., 0.25 mm, and still provide adequate flow volume for the reagent. For a gasket 18 having a central opening 19 of one $cm^2$, the entire active volume may be less than 100 microliters. Typical satisfactory dimensions for the gasket are 0.25 mm thickness with a central square opening approximately 1.5 cm on a side, with a total reaction volume of about 65 microliters, significantly less than that required for flow cells in comparable systems.

The press block 13 is preferably formed of a strong and non-reactive synthetic material, e.g., Kel-F® chlorotrilfluoroethylene polymer from Minnesota Mining and Manufacturing Company, in a block with an engagement surface 20 lapped flat. The standing frame 22 may be formed of metal, e.g., aluminum. Various other materials may be utilized for the parts of the flow cell.

In preparation for use of the flow cell, the base 11 may be fixed in position to a mounting ring (not shown) on an optical breadboard. The base is preferably formed such that the registration surface 22 is in a precise location with respect to the optical system so that the active surface 16 of the substrate is at a focal point within a few microns. The standing frame 12 is secured to the base 11 utilizing the set screw 25, and the substrate 15 is then mounted in position onto the base 11 so as to cover the central opening 21 and be in full engagement (at its surface 17) with the registration surface 22. The gasket 18 is then positioned on the active surface 16 of the substrate so that the central opening 19 in the gasket is fully within the window opening 21 of the base at a proper position, and the press block 13 is then positioned over the gasket 18 so that the engagement surface 20 properly seats against the gasket 18. The standing frame 12 preferably includes a flat machined upright surface 58 against which a flat side 59 of the press block 13 may be engaged to locate the press block in proper position. An edge of the substrate 15 may also be engaged against the flat surface 58 to conveniently locate the substrate in a proper position. Accurate positioning of the gasket 18 may be readily facilitated in this manner by placing the gasket 18 onto the engagement surface 20 of the press block, after which the press block and gasket are then engaged with the substrate 15 with the press block surface 59 located against the upright surface 58.

If desired, two or more of the flow cells 10 may be connected together, such that reagent flowing out of one flow cell flows into another flow cell. In this way, several substrates may be treated simultaneously, while minimizing the use of the reagent.

It is understood that the invention is not confined to the particular embodiments set forth herein as illustrative, but embraces all such modified forms thereof as come within the scope of the following claims.

What is claimed is:

1. A flow cell of the type that may be used in the synthesis of arrays of DNA probes and the like, comprising:
    (a) a base having a central window opening and a registration surface against which a substrate with an active surface may be mounted;
    (b) a gasket having a central opening defining an active area surrounded by material of the gasket, an inlet extension opening extending from the central opening, and an outlet extension opening extending from the central opening of the gasket, the gasket mountable on a substrate which is mounted on the base;
    (c) a press block having an engagement surface which may be engaged against the gasket to press the gasket against a substrate mounted on the base; and
    (d) means for pressing together the press block, gasket, and substrate to the base to form a sealed volume defined by the periphery of the openings in the gasket and the active surface of the substrate and the engagement surface of the press block, and an inlet channel in the press block extending from an exterior surface thereof to communication with the inlet extension opening in the gasket and an outlet channel in the press block extending from communication with the outlet extension opening in the gasket to an external surface of the press block.

2. The flow cell of claim 1 wherein the registration surface of the base is raised above adjacent areas of the base and surrounds the central window opening in the base, the registration surface formed flat to allow the precise location of the active surface of a transparent substrate to be defined with respect to an optical image projected onto the substrate through the window opening of the base.

3. The flow cell of claim 2 further including a reference surface on the base that is parallel to the registration surface whereby the base can be mounted with the reference surface against a surface of an image former to thereby locate the parallel registration surface.

4. The flow cell of claim 1 wherein the gasket is formed of a thin, non-reactive material having parallel opposite flat surfaces.

5. The flow cell of claim 4 wherein the gasket thickness is less than one mm.

6. The flow cell of claim 4 wherein the total volume enclosed by the central opening of the gasket between the engagement surface and the substrate surface is less than 100 microliters.

7. The flow cell of claim 6 wherein the thickness of the gasket is about 0.25 mm.

8. A flow cell of the type that may be used in the synthesis of arrays of DNA probes and the like, comprising:
  (a) a base having a central window opening and a registration surface against which a substrate with an active surface may be mounted;
  (b) a gasket having a central opening defining an active area surrounded by material of the gasket, an inlet extension opening extending from the central opening, and an outlet extension opening extending from the central opening of the gasket, the gasket mountable on a substrate which is mounted on the base;
  (c) a press block having an engagement surface which may be engaged against the gasket to press the gasket against a substrate mounted on the base; and
  (d) means for pressing together the press block, gasket, and substrate to the base to form a sealed volume defined by the periphery of the openings in the gasket and the active surface of the substrate and the engagement surface of the press block including a standing frame secured to the base having an upright section extending from the base and an arm section extending from the upright section over the window opening in the base, and a press screw threadingly engaged with the arm section with a drive end thereof positioned to engage against an external surface of the press block as the press screw is turned to thread it toward the press block, and an inlet channel in the press block extending from an exterior surface thereof to communication with the inlet extension opening in the gasket and an outlet channel in the press block extending from communication with the outlet extension opening in the gasket to an external surface of the press block.

9. The flow cell of claim 8 wherein the drive end of the press screw is rounded.

10. The flow cell of claim 9 wherein the external surface of the press block opposite to the engagement surface has a concave depression formed therein which is fitted to receive the rounded drive end of the press screw to form a ball-and-socket engagement.

11. A flow cell of the type that may be used in the synthesis of arrays of DNA probes and the like, comprising:
  (a) a base having a central window opening and a registration surface against which a substrate with an active surface may be mounted;
  (b) a press block having an engagement surface such that a substrate with an active surface can be engaged between the press block and the registration surface of the base;
  (c) a press comprising a standing frame secured to the base and having an upright section extending from the base and an arm section extending from the upright section over the central window opening in the base, and a press screw threadingly engaged with the arm section and positioned to engage an external surface of the press block with a drive end thereof as the press screw is turned to thread it toward the press block.

12. The flow cell of claim 11 further including a gasket having a central opening defining an active area surrounded by the material of the gasket, an input extension opening extending from the central opening and an output extension opening extending from the central opening, the gasket mountable on the substrate between the substrate active surface and the engagement surface of the press block.

13. The flow cell of claim 12 wherein the press block includes an inlet channel extending from an external surface to communication with the inlet extension opening in the gasket and outlet channel in the press block extending from communication with the outlet extension opening in the gasket to an external surface of the press block.

14. The flow cell of claim 11 wherein the registration surface of the base is raised above adjacent areas of the base and surrounds the central window opening in the base, the registration surface formed flat to allow the precise location of the active surface of a transparent substrate to be defined with respect to an optical image projected onto the substrate through the window opening of the base.

15. The flow cell of claim 14 further including a reference surface on the base that is parallel to the registration surface whereby the base can be mounted with the reference surface against a surface of an image former to thereby locate the parallel registration surface.

16. The flow cell of claim 11 wherein the gasket is formed of a thin, non-reactive material having parallel opposite flat surfaces.

17. The flow cell of claim 16 wherein the gasket thickness is less than one mm.

18. The flow cell of claim 16 wherein the total volume enclosed by the central opening of the gasket between the engagement surface and the substrate surface is less than 100 microliters.

19. The flow cell of claim 18 wherein the thickness of the gasket is about 0.25 mm.

20. The flow cell of claim 11 wherein the drive end of the press screw is rounded.

21. The flow cell of claim 20 wherein the external surface of the press block opposite to the engagement surface has a concave depression formed therein which is fitted to receive the rounded drive end of the press screw to form a ball-and-socket engagement.

* * * * *

UNITED STATES PATENT AND TRADEMARK OFFICE
CERTIFICATE OF CORRECTION

PATENT NO. : 6,315,958 B1
DATED : November 13, 2001
INVENTOR(S) : Singh-Gasson et al.

It is certified that error appears in the above-identified patent and that said Letters Patent is hereby corrected as shown below:

Column 8,
Line 48, please change the word from "the gasket" to -- a gasket --

Signed and Sealed this

Twentieth Day of July, 2004

JON W. DUDAS
*Acting Director of the United States Patent and Trademark Office*